(12) United States Patent
Croze et al.

(10) Patent No.: US 6,274,156 B1
(45) Date of Patent: Aug. 14, 2001

(54) AGROCHEMICAL COMPOSITIONS IN THE FORM OF DISPERSABLE GRANULES

(75) Inventors: Ernest Croze, Bron; Martine Gautier, Limonest, both of (FR)

(73) Assignee: Rhone-Poulenc Agrochimie, Lyons (FR)

( * ) Notice: Subject to any disclaimer, the term of this patent is extended or adjusted under 35 U.S.C. 154(b) by 0 days.

(21) Appl. No.: 09/323,278

(22) Filed: Jun. 1, 1999

Related U.S. Application Data

(63) Continuation of application No. 08/854,273, filed on May 9, 1997, now abandoned, which is a continuation of application No. 08/366,106, filed on Dec. 29, 1994, now abandoned.

(30) Foreign Application Priority Data

Dec. 29, 1993 (FR) .................................................. 93 16020

(51) Int. Cl.[7] ............................... A01N 25/12; A61K 9/46
(52) U.S. Cl. ............................................... 424/405; 424/43
(58) Field of Search ...................................... 424/405, 43

(56) References Cited

U.S. PATENT DOCUMENTS 2,999,293  9/1961  Taff et al. ............................... 424/44

FOREIGN PATENT DOCUMENTS

| | | |
|---|---|---|
| 0391851 | 10/1990 | (EP) . |
| 0544602 | 6/1993 | (EP) . |
| 4-226901 | 8/1992 | (JP) . |
| 93/22215 | 11/1993 | (WO) . |

OTHER PUBLICATIONS

Chemical Patents Index, Documentation Abstracts Journal, Section Ch, Week 9239, AN 320859 (Sankyo Co. Ltd.), Aug. 17, 1992.

Chemical Patents Index, Documentation Abstracts Journal, Section Ch, Week 9320 (Hokko Chem. Ind.), Apr. 20, 1993.

*Primary Examiner*—Peter F. Kulkosky
(74) *Attorney, Agent, or Firm*—Burns, Doane, Swecker & Mathis, L.L.P.

(57) ABSTRACT

A solid concentrated agrochemical composition comprising a homogeneous mixture of: (1) one (or a number of) concentrated compositions A in the form of dispersible granules, each granule containing at least one active material and not containing an effervescent agent, and having a cumulative pore volume of between 0.17 and 0.35 ml/g and having an apparent density of between 0.35 and 0.8 g/cm$^3$; and (2) a concentrated composition B in the form of dispersible granules, each granule containing an effervescent agent and not containing an active material, and having a cumulative pore volume of between 0.020 and 0.13 ml/g and having an apparent density of between 0.8 and 1.5 g/cm$^3$; the A/B quantitative ratio being between 0.01 and 30.

A containerization system comprising said agrochemical composition within a bag whose wall is a film consisting of a film-forming material which is soluble or dispersible in water.

39 Claims, No Drawings

AGROCHEMICAL COMPOSITIONS IN THE FORM OF DISPERSABLE GRANULES

This application is a continuation of application Ser. No. 08/854,273, filed May 9, 1997 abandoned, which in turn is a continuation of application Ser. No. 08/366,106, filed Dec. 29, 1994, abandoned.

The subject of the present invention is a new agrochemical composition and a containerization system comprising the said composition.

Containerization systems are known, especially by European Patent Publication No. EP 0544602, comprising effervescent dispersible granules of a material which is active in agriculture placed in a bag, the wall of which is a film consisting of a film-forming material which is soluble or dispersible in water. Such systems offer the user, especially the farmer, a much appreciated convenience of use and especially the possibility of quickly obtaining, and without specific stirring means, a homogeneous spray liquid (known as slurry) while making possible high safety of use.

However, such granules are usually manufactured by so-called dry agglomeration or granulation techniques, that is to say without solvent and especially without water. Such techniques make it desirable to prepare, prior to the granulation, a very fine powder, that is to say a powder whose constituent particles have a size of between 6 and 30 $\mu$m and preferably between 8 and 20 $\mu$m. Now, these powders are capable of coming into contact either directly with the skin of the people who are handling them or, after their accidental suspension in the air in the form of clouds, with the upper respiratory tracts of these same people. Such contacts can occur with the operators present in an industrial plant, during possible escapes when mixers are opened, or alternatively with the operators who carry out cleaning of the equipment, whether mixers or granulators, or alternatively with the operators who carry out the sampling necessary for monitoring the manufacturing process. Now, it is desirable to limit as far as possible, indeed to entirely prevent, any contact of this type in the case of active materials which can exhibit a risk of toxicity, in order to ensure the safety of the operators and to guarantee the cleanliness of the manufacturing sites.

Moreover, the intimate contact in these granules between the active material, which can have traces of residual moisture, and the effervescent agent, which is hygroscopic, is often harmful to the behaviour on storage, that is to say to maintaining the required qualities of the granules, especially regarding their ability to effervesce, due to passivation phenomena.

Japanese Patent Application 4-226901, published on Aug. 17, 1992, indeed mentions a soluble sachet containing dispersible granules of active material, on the one hand, and effervescent granules without active material, on the other hand, which can contribute to reducing these passivation phenomena. However, the dispersible granules described are manufactured by compacting with rollers, which is a dry granulation technique, so that this patent application entirely ignores the critical importance of the problem to be solved, which is related to the industrial hygiene conditions of the manufacture of the product.

An object of the present invention is to make available agrochemical compositions whose manufacture presents a decreased risk for the workers.

Another object of the present invention is to make available agrochemical compositions which are easier to manufacture.

Another subject of the present invention is an improvement in the behaviour on storage of the agrochemical compositions.

Another object of the present invention is to make available to farmers concentrated agrochemical compositions which make it possible, after dilution with water, to easily and quickly obtain a homogeneous spray liquid.

Another object of the present invention is to make available to farmers concentrated agrochemical compositions whose handling offers improved safety.

Another object of the present invention is to make available to the user a concentrated agrochemical composition in a soluble sachet whose rate of dissolution in water is increased.

It has now been found that these aims could be achieved in all or in part by virtue of the compositions and containerization systems according to the invention.

In the present invention, the percentages indicated are percentages by weight, unless otherwise specified, and active materials are understood to mean materials which are active in agriculture such as plant protection agents, agrochemical products, pesticides, growth regulators or plant nutrient agents. The pesticides are more particularly herbicides, insecticides, fungicides, nematicides and acaricides.

Apparent density within the meaning of the present invention is essentially the ratio of the weight of a specific amount of granules to the volume occupied by these same granules after settling carried out under standard conditions, that is to say under the following conditions: 80 g of on-test granules are poured into a 250 cm$^3$ measuring cylinder which is subjected to 50 periodic movements composed of a movement from the bottom upwards with an amplitude of 2.5 cm followed by a movement from the top downwards of the same amplitude. Each period lasts 2 seconds. At the end of the operation, the volume occupied by the granules in the measuring cylinder is noted, enabling the apparent density of the granules to be deduced.

The first subject of the present invention is agrochemical compositions which are solid concentrated compositions, characterized in that they are a homogeneous mixture:
  of one (or a number of) concentrated compositions A in the form of dispersible granules, each granule containing at least one active material and not containing an effervescent agent, and having a cumulative pore volume of between 0.17 and 0.35, preferably between 0.20 and 0.30, ml/g and having an apparent density of between 0.35 and 0.8, preferably between 0.4 and 0.7, g/cm$^3$; and
  of a concentrated composition B in the form of dispersible granules, each granule containing an effervescent agent and not containing an active material, having a cumulative pore volume of between 0.020 and 0.13, preferably between 0.025 and 0.10, ml/g and having an apparent density of between 0.8 and 1.5 g/cm$^3$, preferably between 1.0 and 1.4 g/cm$^3$;
  the A/B quantitative ratio being between 0.01 and 30, preferably between 0.05 and 10 and more preferentially still between 0.08 and 5.

The cumulative pore volume of the granules according to the invention is measured using a mercury porosimeter according to techniques known per se.

Dispersible granule is understood to mean a solid and cohesive agglomerate of constituent particles which have a size of between 1 and 20 $\mu$m, which agglomerate, after mixing with water, disintegrates or disperses to give a homogeneous and stable suspension. Presentation as a dispersible granule offers the user great convenience of use which makes them very desirable.

The possibilities of chemical reaction between the effervescent agent of the solid composition B and possible residual moisture in the active material of the solid composition A are very greatly restricted due to the very low exchange surface area between these two granulated solid compositions, so that the result thereof is a behaviour on storage of the composition according to the invention which is greatly improved.

The difference in the porosity characteristics between the dispersible granules containing the active material(s) and the effervescent dispersible granules which do not contain them is particularly advantageous in promoting an improved dispersion of the agrochemical composition according to the invention. In fact, water more rapidly penetrates inside granules containing the active material(s), despite the strongly hydrophobic nature of the active materials used in practice, and the effervescent inert granules more efficiently contribute to the rapid disintegration of the dispersible granules of active material.

According to an advantageous aspect of the invention, the material which is active in agriculture which can be used in the dispersible granules of the composition A is a pesticide, preferably an insecticide, a nematicide or an acaricide. It is in fact always desirable, even for a material which is active in agriculture which is known to present no danger for the user, to protect the process worker liable to be frequently in contact with very fine powders containing the said active material for a long period, for example a period greater than 1 month and preferably greater than 1 year.

According to another advantageous aspect of the invention, the active material which can be used in the dispersible granules of the composition A has an $LD_{50}$ of less than 2000 mg/kg, preferably of less than 1550 mg/kg and more preferentially still of less than 500 mg/kg. The $LD_{50}$ is a measurement of the acute dermal toxicity obtained by determining the amount (lethal dose) of active material which, when it is applied to the skin of an animal, induces 50% mortality in the group of animals thus treated. The $LD_{50}$ is expressed by weight of active material applied with respect to the unit of weight of the animal treated, i.e. in mg per kg. The $LD_{50}$ and the acute dermal toxicity vary inversely, that is to say that a low $LD_{50}$ corresponds to a high acute dermal toxicity and vice versa. The animal chosen in either the rat or the rabbit and, more precisely, that of these 2 animals which leads to the lower $LD_{50}$, in other words the animal which is the more sensitive to the substance whose acute dermal toxicity it is desired to measure. The protocol followed for exactly determining the $LD_{50}$ is Method No. 402 of the "Lignes directrices de l'OCDE pour les essais de produits chimiques" [OECD Guidelines for Testing Chemical Products], a work published by the OCDE (Organization for Economic Cooperation and Development), 1987 edition. This characteristic of the invention is particularly advantageous in that the corresponding compositions which are the subjects of the invention can then be prepared without there being any risk of contact, for the operators present in the manufacturing plant, with very fine powders of active material whose high acute dermal toxicity is liable to threaten the good health of the said operators.

According to another advantageous aspect of the invention, the dispersible granules which can be used in the compositions A and B according to the invention have a median diameter of between 0.150 and 10 mm and preferably between 0.200 and 4 mm. Median diameter is understood to mean the median value of the particle size distribution curve of the granules, which is measured by the following method: 50 g of granules to be analysed are passed through a stack of 10 superimposed sieves with a mesh size ranging from 5 mm to 0.074 mm. After sieving for 10 min, the residues retained on each sieve are weighed individually and expressed as percentage relative to the mass of granules analysed. The said percentages of residues are regarded as being distributed according to a normal law, also known as the Gaussian distribution, from which the median value equal to the median diameter of the granules analysed is calculated. The ability of these granules to flow easily, like liquids, is particularly appreciated by farmers for the preparation of a spray liquid as well as by manufacturing workers for their packaging. Moreover, the container containing such granules no longer contains, after being emptied, any residue which adheres to the walls and to the bottom liable to pollute the environment or to cause difficulties to people responsible for destroying or recycling these containers.

According to another, also advantageous, aspect of the invention, the dispersible granules of the composition according to the invention are characterized in that their minimum size is greater than 0.05 mm and preferably greater than 0.15 mm. The minimum size of the granules is measured, depending on the order of magnitude of this size, either by a dry sieving method or by a wet sieving method or alternatively by an optical method, for example by laser beam diffraction. Such granules do not present the risk of forming a dispersion in the air in the form of a cloud and thus of coming into contact with the skin of the people who are handling them or alternatively of entering into their upper respiratory tracts.

According to another aspect of the invention, the solid concentrated composition of the invention is characterized in that the median diameter of the granules of the composition A/median diameter of the granules of the composition B ratio is less than or equal to 5 and preferably less than or equal to 2. In this case, the solid concentrated composition is more stable, as regards the homogeneity of the mixture on storage and transportation, so that the farmer can use the said composition, contained in its container, a number of times, in other words by making successive withdrawals of the product. Each of the amounts thus withdrawn then has the same structure and the same properties as the whole of the composition placed in its container.

According to another aspect of the invention, the content of active material or of active materials in the concentrated composition(s) A is between 5 and 100% and preferably between 50 and 90%. The possibility of having available agrochemical compositions containing a high active material content thus makes it possible to reduce the volume of marketed product to be stored or transported and thus to bring about a reduction in the corresponding costs.

According to another aspect of the invention, the effervescent agent of the composition B advantageously consists of a pair of products such as a carbonate (or, preferably alkaline, hydrogencarbonate) and an acid (preferably solid and weak). The acid/carbonate ratio by weight is generally between 0.3 and 30 and preferably between 0.5 and 15.

The alkaline carbonate can be derived from an alkali metal (especially sodium or potassium) or alkaline-earth metal (calcium or magnesium), or from an ammonium or organoammonium cation (carbonate derived from a primary, secondary or tertiary amine or from a quaternary ammonium cation), but is preferably derived from an alkali metal.

The solid and weak acid is advantageously a carboxylic or polycarboxylic or phosphoric or phosphonic acid or one of their salts or esters containing an acidic functional group.

According to another aspect of the invention, the content of effervescent agent in the concentrated composition B is between 3 and 95% and preferably between 5 and 60%.

According to another aspect of the invention, the dispersible granules of the compositions A and B additionally comprise:

from 0.1 to 10% and preferably from 0.5 to 5% of a wetting agent, that is to say of a compound which makes it possible for the granule to quickly enter into the water, from 0.3 to 25% and preferably from 2 to 20% of a dispersing agent, that is to say of a compound which provides for the particles to be held in suspension in the slurry of use, and from 0 to 90% and preferably from 0 to 30% of a vehicle or filler which is soluble or insoluble in water.

Mention may be made, as compounds which can be used as wetting agent, of, for example, salts of alkylarylsulphonate type, especially alkali metal alkylnaphthalenesulphonates, salts of polycarboxylic acids, polycondensates of ethylene oxide with fatty alcohols or with fatty acids or with fatty amines, substituted phenols (especially alkylphenols or arylphenols) or salts of esters of sulphosuccinic acids.

Mention may be made, as compounds which can be used as dispersing agent, of, for example, polymers of arylsulphonate type, especially the alkali metal polynaphthalenesulphonates obtained by condensation of (alkyl) arylsulphonates with formaldehyde, lignosulphonates, polyphenylsulphonates, salts of polyacrylic acids, salts of lignosulphonic acids, salts of phenolsulphonic or naphthalenesulphonic acids, taurine derivatives (especially alkyltaurates), phosphoric esters of polyoxyethylenated phenols or alcohols, esters of fatty acids and of polyols, or the derivatives of the above compounds containing sulphate, sulphonate and phosphate functional groups.

The vehicle of the dispersible granules of the compositions A and B is a natural or synthetic, organic or inorganic solid material. This vehicle is generally inert and acceptable in agriculture, especially on the treated plant. It can be chosen, for example, from clay, diatomaceous earth, natural or synthetic silicates, silica, resins, waxes, solid fertilizers, soluble or insoluble inorganic salts, organic derivatives, or polysaccharide compounds such as starch, cellulose, sugars or lactose.

Preference is given, among the vehicles which can be used, to hydrophilic vehicles having a disintegrating action, that is to say facilitating the breakup of the granule into its constituent particles in the presence of water. Mention may be made, as compounds of this type, of bentonites (natural or activated), starch and its derivatives (especially alkyl starches and carboxyalkyl starches), celluloses (especially microcrystalline cellulose) and cellulose derivatives (especially carboxyalkyl cellulose), alginates, soluble inorganic salts or crosslinked polyvinylpyrrolidone.

The dispersible granules of the compositions A and B can contain, in addition to the constituents indicated above, other compounds, especially compounds more specifically having a binding action, that is to say a compound of polymeric type which is helpful to the cohesion and use of the granules. These compounds possessing a binding action can either be compounds which are distinct from those mentioned above or else they can be these same compounds in so far as they are capable of having a two-fold action. It is preferable to use, as compounds or agents of this type, agents such as gums, especially gum arabic; adhesives, especially dextrin; sugars, especially glucose and lactose; cellulose derivatives, especially alkyl cellulose and carboxyalkyl cellulose; starch; flour; polymers, especially polyvinylpyrrolidone, poly(vinyl alcohol), polyethylene glycol, polyacrylate or poly(vinyl acetate); soluble waxes or alkali metal silicates.

The binding agent and the agent or vehicle possessing disintegrating properties do not have conflicting effects in so far as the action of the binding agent is exerted in the solid state to bind together the various solid particles of the compositions according to the invention and as the action of the agent possessing disintegrating properties is exerted in the liquid state when the compositions according to the invention are dispersed in water.

In addition further to the constituents described above, the dispersible granules of the compositions according to the invention can contain antifoaming agents, densifying agents, sequestering agents, stabilizing agents, penetrating agents, preserving agents, adhesives, anticaking agents, dyes and others.

Of course, the dispersible granules of the compositions according to the invention can further contain all the solid or liquid additives corresponding to the usual techniques of agrochemical formulation.

It is additionally preferable, among the constituents of any nature of the dispersible granules according to the invention, to choose those which, by their nature and their dose, provide granules having:

a wettability time, as defined below, of less than 5 min and preferably of less than 2 min, a degree of dispersibility, as defined below, greater than 85% and preferably greater than 92%, and a degree of suspensibility, as defined below, greater than 50% and preferably greater than 70%.

The granules possessing these characteristics make possible a particularly easy preparation of the spray liquid by the farmer and give rise to a spraying of the active material (s) which provides a uniform distribution of the latter on the surface to be treated.

The wettability time is measured according to the MT 53.3.1 technique described in the Cipac Handbook, Volume 1, pages 966–967 edited by G. R. Raw in 1970. It consists essentially in measuring the wettability time of 5 g of granule poured into 100 ml of water.

The degree of dispersibility is measured according to the following technique. 10 g of granule are poured into a 250 ml measuring cylinder containing 250 ml of hard water defined in the method 18.1.4 described in the Cipac Handbook, Volume 1, pages 875–878, edited by G. R. Raw in 1970. The measuring cylinder and its contents are inverted 10 times and a sieving is then carried out by pouring the contents of the measuring cylinder through a sieve with a mesh size equal to 160 $\mu$m. The residue is dried and weighed. The degree of dispersibility is then expressed by the percentage of granule passing through the sieve.

The degree of suspensibility is measured according to the MT 15.1. technique, Note 4, described in the Cipac Handbook, Volume 1, pages 861–865, edited by G. R. Raw in 1970. It consists essentially in pouring 2.5 g of granule into a 250 ml measuring cylinder containing 250 ml of hard water, in inverting the measuring cylinder and its contents 30 times, in allowing to stand for 30 min and in measuring the mass of material contained in the bottom 25 ml (10% of the volume of the measuring cylinder) of the measuring cylinder; the degree of suspensibility is then expressed by the percentage of material remaining in suspension in the upper 90% of the measuring cylinder.

The agrochemical compositions which are the subjects of the invention are prepared by simple mixing of the compositions A and B by any process which makes possible homogeneous mixing of these compositions in the desired proportions, such as a ribbon blender, a mixer or a drum rotating around an oblique axis.

The dispersible granules of the composition A are prepared according to the following particularly advantageous process.

In a first stage, the active material in the form of a coarse powder, for example of a powder whose particles have a size of between 40 μm and 2 cm and preferably between 50 μm and 0.5 cm, is mixed with water and the necessary additives so as to form a fluid paste. This fluid paste, whose water content is from 20 to 70% and preferably from 30 to 50%, is then subjected to a first milling by means of a mill such as a colloid mill or a hammer mill, so as to bring the amount of particles whose size exceeds 160 μm to less than 20% and preferably to less than 10%. The resulting mixture is then again subjected to one or a number of milling stages by passing through a bead mill, the beads used having a size of between 0.8 and 2 mm. A suspension concentrate is then obtained whose suspended particles have a size of between 1 and 7 μm and preferably of between 1.5 and 5 μm. Some soluble additives, such as some thickening agents, are optionally introduced into the suspension concentrate at this stage.

In a second stage of the preparation of the dispersible granules of the composition A, the solid particles present in the suspension thus prepared are then agglomerated according to two possible embodiments.

According to the first embodiment of the agglomeration of this second stage, the suspension is sprayed in the form of droplets into a hot air dryer also known as an atomizer or spray tower. The water contained in the suspended droplets rapidly evaporates on contact with the air, leading to the agglomeration of the solid particles and to the formation of fine and dry granules. The temperature of the drying air is generally between 120 and 300° C. and preferably between 150 and 250° C. After sieving and partial recycling, the granules obtained have a median diameter, as defined above, of between 0.150 and 10 mm and preferably of between 0.200 and 4 mm.

According to a second embodiment of the agglomeration of this second stage, a mixture of the solid ingredients of the granule, other than the active material, is first prepared. This mixture is air-jet milled so as to obtain a very fine powder whose solid particles have a median diameter of between 5 and 15 μm. This very fine powder is then mixed, for example in a ribbon blender, with the aqueous suspension containing the active material prepared in the first stage. A wet powder is obtained, the water content of which is between 10 and 40% and preferably between 15 and 35%, which is then granulated by extrusion through a die. The granules thus prepared are dried in a fluid bed drier at a temperature of between 60 and 120° C.

These processes for the preparation of the dispersible granules of the composition A are particularly advantageous in that at no point in the process is it necessary to handle very fine powders of material which is active in agriculture, that is to say an assembly of particles with a size of between 6 and 30 μm and preferably between 8 and 20 μm liable to come into contact with the operators, especially with the upper respiratory tracts of the latter.

The dispersible granules of the composition B are prepared by dry agglomeration (especially without solvent) of the constituents of the effervescent composition ground to the form of a powder with particles of a size of between 5 and 20 μm. Dry agglomeration is carried out by a compacting, or sintering, technique, preferably at room temperature or at least below 50° C. The device used for this technique is preferably composed of two cylinders rotating about parallel axes applied very tightly against one another and each driven by a rotational movement in the opposite direction.

Another subject of the present invention is a containerization system comprising:

a) a solid concentrated agrochemical composition according to the present invention,
b) a bag whose wall is a film consisting of a film-forming material which is soluble or dispersible in water,
the said bag being closed and containing the said composition.

Material which is dispersible in water is to be understood as meaning a material which, under the effect of normal stirring (such as commonly practised by farmers in spray tanks), leads to a dispersion of fine particles with a size of less than 40 μm and preferably less than 15 μm.

According to an advantageous aspect of the invention, the amount of composition according to the invention present in a containerization system as defined above is an amount effective for treating a given region of cultivated or uncultivated ground.

According to an advantageous aspect of the containerization system according to the invention, the median diameter of the composition A/median diameter of the composition B ratio is greater than 5 and preferably greater than 2. In fact, in this case, the absence of homogeneity of the composition resulting from storage and transportation does not pose a problem due to the practical use of the containerization system as described later in the present text, especially because the farmer does not withdraw successive amounts of the said composition but uses it just once.

According to another preferred aspect of the invention, the density of the containerization system according to the invention is greater than 1 and preferably between 1.005 and 2, so that when the containerization system is introduced into the water-filled spray tank, all its surface is in contact with the water in a shorter time. In addition, the speed of dispersion of the solid ingredients, especially the active material of the composition A is particularly high, especially because contact between the water and the composition according to the invention is improved, and also because the gas bubbles resulting from the effervescence contribute to the disintegration of the sachet and to the acceleration of the dispersion of the granules in the water.

For the purpose of producing such containerization systems with a density greater than 1, it is preferable to use compositions B according to the invention additionally comprising a densifying agent. Densifying agent is to be understood as meaning an inorganic or organic filler or vehicle with a density of between 1.2 and 8.

Such fillers are preferably chosen from barium or titanium salts and, even more preferably, from one of the following compounds: barium sulphate or titanium monoxide.

The amount of densifying agent chosen can represent, according to the situation, from 30 to 90% and preferably from 50 to 85% of the total of the composition B.

For the purpose of improving contact between the water of the spray tank and the containerization system according to the invention and/or the composition according to the invention, containerization systems which are free of gas pockets are preferably used. These containerization systems are generally such that, when the bag is sealed, it is not possible to see the least space between the effervescent composition in the pulverulent form and the wall of the bag and/or that it is not possible manually to lift off the wall of the bag from the pulverulent material. This therefore corresponds to an absence of air pockets or, in other words, to a maximum degree of filling for the form under consideration of the bag. In practice, it is advantageous to fill the bags of the invention under an absolute pressure below 200 millibar and preferably below 150 millibar, so as to ensure adherence of the film to the effervescent composition at the time of packing into the bag and before final sealing of the bag, and even up to final use of the containerization systems according to the invention, even after storage.

According to another aspect of the invention, the bag made of film-forming material contains the composition according to the invention with an atmosphere such that the amount of water present in this atmosphere is less than 4 mg per liter and preferably less than 3 mg per liter. The volume of the atmosphere in the bag is equal to the internal volume of the bag less the volume of the granules without the interstices between these granules.

According to another aspect of the invention, the amount of composition according to the invention contained in the bag is between 1 g and 3 kg and preferably between 5 g and 1 kg. It is an advantage of the invention, compared with pellets and tablets known in the prior art, that it is possible to put, in the same container, much more significant amounts of active material into a unit handled by the farmer.

According to another aspect of the invention, the film-forming material, which is soluble or dispersible in water, constituting the wall of the bag can be of widely varying type. It is preferably soluble in water. It is generally a polymeric material, such as poly(ethylene oxide), poly(ethylene glycol), starch or modified starch; alkylcellulose or hydroxyalkylcellulose, such as hydroxymethylcellulose, hydroxyethylcellulose or hydroxypropylcellulose; carboxymethylcellulose; poly(vinyl ether)s, such as poly(methyl vinyl ether) or poly(2-methoxyethoxyethylene); poly(2,4-dimethyl-6-triazinylethylene); poly(3-morpholinylethylene); poly(N-1,2,4-triazolylethylene); poly(vinylsulphonic acid); polyanhydrides; low molecular weight melamine/formaldehyde or urea/formaldehyde resins; poly(2-hydroxyethyl methacrylate); poly(acrylic acid) and its homologues.

The preferred materials to constitute the bags are poly(ethylene oxide), methylcellulose and poly(vinyl alcohol) (PVA). A preferred material to constitute the walls of the bag is poly(vinyl alcohol). When PVA is used, a poly(vinyl acetate) (or another vinyl ester), partially or totally hydrolysed or alcoholysed, that is to say 40–100%, preferably 80–99%, hydrolysed or alcoholysed, is preferably used. Copolymers or other derivatives of these polymers can also be used.

According to another aspect of the invention, the bag containing the composition according to the invention comprises a first nonplanar film made of material which is soluble or dispersible in water, this first film being adjacent to a second film, itself made of material which is soluble or dispersible in water, along a continuous sealing line uniting these two films, the said line constituting a closed line which is not intersected and which delimits an essentially planar region.

According to another aspect of the invention, the bag containing the composition according to the invention consists of a single film, and preferably comprises at least three sealing regions, two of which are substantially rectilinear and coplanar and cut by the third into two substantially isolated regions.

According to a variant of the invention, the containerization systems described above can additionally comprise an external container. This external container has walls consisting of a system containing at least two layers adhesively bonded to each other, one made of flexible cardboard paper, called "kraft-liner", and the other made of polyethylene. This two-layer system can additionally comprise a third layer adhesively bonded to the polyethylene and consisting of aluminium.

The containerization systems according to the invention are prepared according to packaging techniques known per se. By virtue of the presentation of the composition according to the invention in the form of dispersible granules, the bagging is easier to carry out due to the ability of the granules to flow. The amount by weight of solid concentrated agrochemical composition according to the invention, introduced into a sachet, is advantageously controlled with improved accuracy, due to the virtually constant nature presented by the apparent density of the granules with respect to their settling state, especially in comparison with the apparent density of a powder.

The containerization systems according to the invention are used in practice by placing them into tanks containing water; these tanks can optionally be subjected to stirring and can, in certain cases, be carried on the backs of the users. The mixture thus obtained, known as spray slurry, can be used as it is for applying to the cultivated or uncultivated surfaces to be treated. The containerization systems according to the invention can also be used, in the case of a treatment in a flooded rice paddy, simply by throwing on to the water surface of the rice paddy.

The examples below are given solely by way of illustration and without implied limitation of the containerization systems and compositions according to the invention.

In these examples, all the effervescent granules mentioned have a cumulative pore volume of between 0.025 and 0.10 ml/g. All the granules containing one or a number of active materials have a cumulative pore volume of between 0.20 and 0.30 ml/g and an apparent density of between 0.4 and 0.6 g/cm$^3$.

EXAMPLE 1

1A) 200 g of effervescent granule without active material are manufactured in the following way. 420 g of a powder obtained by dry mixing the following ingredients in the form of pulverulent solids (the size of which is between 50 µm and 1 mm), according to the proportions indicated, are prepared:

| | |
|---|---|
| sodium carbonate | 5% |
| sodium acid pyrophosphate | 50% |
| sodium alkylnaphthalenesulphonate | 3% |
| sodium polyphenylsulphonate | 10% |
| barium sulphate | 32% |

This mixture is air-jet milled to give a powder whose particles have a size of between 5 and 20 µm. This powder is dry agglomerated at room temperature by passing between two cylinders rotating in opposite directions and forced towards one another by the exercise of a force of 2 tonnes per linear centimeter. The ribbon obtained is crushed and sieved to give 200 g of granules with a size of between 0.25 and 0.6 mm and whose apparent density is equal to 1.15 g/cm$^3$.

1B) A granule containing fungicidal active materials is then prepared. To do this, 1600 g of powder are first prepared, this powder being obtained by mixing the following ingredients in the form of pulverulent solids (whose size is between 100 µm and 1 mm), according to the proportions indicated:

| | |
|---|---|
| fosetyl-Al | 45% |
| folpet | 30% |
| cymoxanil | 8% |
| sodium alkylnaphthalenesulphonate | 1% |
| oxyethylenated polyarylphenol | 5% |
| polydimethylsiloxane oil | 0.4% |
| ethoxylated nonylphenol | 0.5% |
| sodium dioctyl sulphosuccinate | 1% |
| sodium lignosulphonate | 9.1% |

The powder obtained is mixed with water so as to obtain an aqueous suspension containing 60% of solid matter. This suspension is subjected to a first milling using a colloid mill. The amount of particles exceeding 160 μm is 6%. The suspension is then subjected to a milling in a bead mill filled to 80% with beads with a size of 1 mm. A size of the particles equal to 5 μm is measured. The suspension is then sprayed in an atomizer whose air temperature is adjusted to 190° C.

After sieving, 800 g of granules with a median diameter equal to 200 μm are collected.

1C) 200 g of granules comprising the effervescent agent prepared above and 800 g of atomized granules containing the active materials are mixed. This mixture is homogenized for 3 minutes in a drum rotating around an oblique axis.

300 g of the above mixture are withdrawn and poured into a tank containing 100 liters of unstirred water. The granules disperse on contact with the water, especially under the effect of the effervescence, and a perfectly homogeneous spray liquid is obtained after 5 minutes.

EXAMPLE 2

2A) In a first step, an effervescent granule without active material is prepared by dry mixing the following ingredients in the form of pulverulent solids, in the following proportions:

| | |
|---|---|
| potassium carbonate | 5% |
| citric acid | 6% |
| sodium alkylnaphthalenesulphonate | 3% |
| sodium polyphenylsulphonate | 10% |
| barium sulphate | 76% |

This mixture is granulated according to the procedure described in Example 1. The apparent density of these granules is equal to 1.3 g/cm³.

2B) In a second step, a dispersible granule containing two herbicidal active materials is then prepared. In order to do this, the preparation is carried out in the following way.

In a first stage, the following solid ingredients, in the form of pulverulent solids (whose size is between 100 μm and 1 mm), are mixed with water according to the following proportions:

| | |
|---|---|
| glyphosate acid | 22.5% |
| oxadiazon | 27% |
| polynaphthalenesulphonate | 5% |
| nonylphenol oxyethylenated with 10 E.O. | 1.5% |
| water | 44% |

This mixture is subjected to a first milling using a colloid mill. The amount of particles exceeding 160 μm is 7%. The suspension is then subjected to a milling in a bead mill filled to 80% with beads with a size of 1 mm. A size of the solid particles of the suspension equal to 5 μm is measured.

In a second stage, a solid premix without active material is prepared by mixing ingredients in the form of pulverulent solids according to the following proportions:

| | |
|---|---|
| ammonium sulphate | 18% |
| lauryl alcohol ethoxylated with 30 E.O. | 13.5% |
| polyphenolic acid | 21% |
| silicoaluminate | 45% |
| silicone oil impregnated to 50% on silica | 2.5% |

This mixture is dry milled with an air jet; the median diameter of the particles is then 7 μm.

In a third stage, 67 g of the suspension prepared in Stage 1 are mixed, in a ribbon blender, with 33 g of solid premix prepared in Stage 2. A wet powder containing 29.5% of water is thus obtained.

In a fourth stage, the wet powder obtained in the preceding stage is extruded through a die and granules are obtained in the form of short cylindrical rods which are dried in a fluid bed at a temperature of 100° C.

2C) The 2 granules thus prepared are then mixed in a proportion of 75% for the granules with active materials and of 25% for the effervescent granules, the mixing being carried out as in Example 1.

1 kg of this mixture is poured into a tank containing 100 liters of unstirred water. Results identical to those of Example 1 are obtained.

EXAMPLE 3

A granule containing the effervescent agent is prepared by dry mixing the following ingredients in the form of pulverulent solids, according to the formula:

| | |
|---|---|
| sodium carbonate | 5% |
| adipic acid | 7% |
| sodium alkylnaphthalenesulphonate | 3% |
| sodium polyphenylsulphonate | 10% |
| barium sulphate | 75% |

This mixture is granulated according to the procedure described in Example 1, the granules obtained having an apparent density of 1.3.

A granule containing active materials is prepared by mixing the following ingredients in the form of pulverulent solids, according to the formula:

| | |
|---|---|
| fosetyl-Al | 80% |
| ethoxylated nonylphenol (40 mol of ethylene oxide) | 5% |
| ethoxylated nonylphenol (10 mol of ethylene oxide) | 1% |
| sodium acetate | 3% |
| sodium lignosulphonate | 5% |
| silicone oil impregnated on silica at 50% | 0.5% |

| -continued | |
|---|---|
| silicoaluminate | 3.5% |
| precipitated silica | 2% |

This mixture is granulated under the same conditions as in Example 1.

The 2 granules thus prepared are then mixed in a proportion of 60% for the granules with active materials and of 40% for the effervescent granules, the mixing being carried out as in Example 1.

500 g of this mixture are introduced into a tank containing 100 liters of unstirred water. Results identical to those of Example 1 are obtained.

EXAMPLE 4

The manufacture of an effervescent granule and of a granule containing an active material is carried out as in Example 1, according to the following formulae:

| effervescent granule | |
|---|---|
| sodium carbonate | 5% |
| citric acid | 7% |
| sodium alkylnaphthalenesulphonate | 3% |
| sodium polyphenylsulphonate | 10% |
| barium sulphate | 75% |

This granule has an apparent density equal to 1.3.

| granule with active material: | |
|---|---|
| 5-amino-1-(2,6-dichloro-4-trifluoromethylphenyl)-3-cyano-4-trifluoromethanesulphinylpyrazole | 80% |
| maleic anhydride-isobutylene copolymer with sodium salt | 6.9% |
| sulphodioctyl succinate | 2% |
| sodium lignosulphonate | 11% |
| silicone oil impregnated on silica at 50% | 0.1% |

The preparation of 5-amino-1-(2,6-dichloro-4-trifluoromethylphenyl)-3-cyano-4-trifluoromethanesulphinylpyrazole is described in European Patent Publication No. EP 0295117. The $LD_{50}$ of this product (on rabbit) is less than 500 mg/kg.

The 2 granules thus prepared are then mixed in a proportion of 10% for the granules with active materials and of 90% for the effervescent granules, the mixing being carried out as in Example 1.

100 g of this mixture are introduced into a tank containing 100 liters of unstirred water. Results identical to those of Example 1 are obtained.

EXAMPLE 5

An effervescent granule without active material identical to that of Example 1 is prepared.

A granule containing an active material and the following various ingredients, according to the proportions indicated, is prepared, the preparation also being carried out as in Example 1:

| aldicarb | 50% |
|---|---|
| sodium alkylnaphthalenesulphonate | 6% |
| sodium lignosulphonate | 8% |
| silicoaluminate | 36% |

The $LD_{50}$ of aldicarb (on rabbit) is 5 mg/kg.

The mixture of the 2 granules is prepared as in Example 1, in a proportion of 15% for the granules with active materials and of 85% for the effervescent granules.

40 g of this mixture are introduced into a sachet made of poly(vinyl alcohol) [poly(vinyl acetate) hydrolysed to 88%] which is soluble in cold water. This sachet was obtained from a single rectangular film which received two perpendicular welding lines. After introduction of the granules, the bag receives a third welding line by heat sealing.

This bag is thrown into a tank containing 100 liters of stirred water. Its density being greater than 1, this bag goes to the bottom of the tank in less than 10 seconds. The water enters into the sachet in less than one minute and the effervescence produced causes shredding of the PVA film, which facilitates its total dissolution, achieved in three minutes. The granules rapidly disperse homogeneously throughout the tank.

EXAMPLE 6

The mixture of Example 4 is introduced into a sachet according to the same method as in Example 5, in a proportion of 10 g. The density of the containerization system obtained is equal to 1.05.

This sachet is thrown into a sprayer with a capacity of 20 liters, which can be attached to the back of the user, and completely filled with water. After one inversion of the sprayer, a perfectly homogeneous spray liquid is obtained.

EXAMPLE 7

An effervescent granule without active material identical to that of Example 2 is prepared.

A granule containing an active material and the following various ingredients, according to the proportions indicated, is prepared, the preparation also being carried out as in Example 1:

| oxadiazon | 30% |
|---|---|
| dioctyl sulphosuccinate | 7% |
| sodium lignosulphonate | 4% |
| carboxymethyl cellulose | 10% |
| silicoaluminate | 49% |

The mixture of the 2 granules is prepared as in Example 1, in a proportion of 20% for the granules with active material and of 80% for the effervescent granules.

By carrying out the introduction as in Example 5, 20 g of this mixture are introduced into a sachet made of poly(vinyl alcohol) which is thrown every meter into a rice paddy covered with water. The sachet dissolves and the granules disperse in 3 minutes, giving rise to a homogeneous distribution of the product in the rice paddy.

EXAMPLE 8

Example 5 is repeated, the granule containing an active material being replaced by the granule obtained according to the proportions indicated:

| | |
|---|---|
| carbaryl | 60% |
| sodium alkylnapththalenesulphonate | 10% |
| sodium lignosulphonate | 6% |
| silicoaluminate | 24% |

Results identical to those of Example 5 are obtained.

EXAMPLE 9

Example 5 is repeated, the granule containing an active material being replaced by the granule obtained according to the proportions indicated:

| | |
|---|---|
| lindane | 55% |
| sodium alkylnaphthalenesulphonate | 10% |
| sodium lignosulphonate | 6% |
| silicoaluminate | 29% |

Results identical to those of Example 5 are obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A solid concentrated agrochemical composition comprising a homogeneous mixture of:
   (1) at least one concentrated composition A in the form of dispersible granules, each granule thereof containing at least one agriculturally active material and being devoid of effervescent agent, and having a cumulative pore volume of between about 0.17 and about 0.35 ml/g and an apparent density of between about 0.35 and about 0.8 g/cm$^3$; and
   (2) a concentrated composition B in the form of dispersible granules, each granule thereof containing an effervescent agent and being devoid of active material, the effervescent agent comprising (a) an alkaline carbonate or hydrogen carbonate and (b) an acid, wherein the acid/carbonate ratio by weight is between about 0.3 and about 30, and the granules of composition B have a cumulative pore volume of between about 0.020 and 0.13 ml/g and an apparent density of between about 0.8 and about 1.5 g/cm$^3$;
   the A/B quantitative ratio is between about 0.05 and about 10; and
   the granules of compositions A and B have a median diameter of between about 0.150 and about 10 mm, and a minimum size greater than about 0.05 mm, the ratio of the median diameter of the granules of composition A to the median diameter of the granules of composition B is less than or equal to about 5, and wherein said agrochemical composition having said pore volume has improved water dispersion characteristics.

2. The composition according to claim 1, wherein the granules of composition A have a cumulative pore volume of between about 0.20 and 0.30 ml/g.

3. The composition according to claim 1, wherein the granules of composition A have an apparent density of between about 0.4 and about 0.7 g/cm$^3$.

4. The composition according to claim 2, wherein the granules of composition A have an apparent density of between about 0.4 and about 0.7 g/cm$^3$.

5. The composition according to claim 1, wherein the granules of composition B have a cumulative pore volume of between about 0.025 and about 0.10 ml/g.

6. The composition according to claim 2, wherein the granules of composition B have a cumulative pore volume of between about 0.025 and about 0.10 ml/g.

7. The composition according to claim 3, wherein the granules of composition B have a cumulative pore volume of between about 0.25 and about 0.10 ml/g.

8. The composition according to claim 4, wherein the granules of composition B have a cumulative pore volume of between about 0.25 and about 0.10 ml/g.

9. The composition according to claim 1, wherein the granules of composition B have an apparent density of between about 1.0 and about 1.4 g/cm$^3$.

10. The composition according to claim 2, wherein the granules of composition B have an apparent density of between about 1.0 and about 1.4 g/cm$^3$.

11. The composition according to claim 3, wherein the granules of composition B have an apparent density of between about 1.0 and about 1.4 g/cm$^3$.

12. The composition according to claim 4, wherein the granules of composition B have an apparent density of between about 1.0 and about 1.4 g/cm$^3$.

13. The composition according to claim 5, wherein the granules of composition B have an apparent density of between about 1.0 and about 1.4 g/cm$^3$.

14. The composition according to claim 6, wherein the granules of composition B have an apparent density of between about 1.0 and about 1.4 g/cm$^3$.

15. The composition according to claim 7, wherein the granules of composition B have an apparent density of between about 1.0 and about 1.4 g/cm$^3$.

16. The composition according to claim 8, wherein the granules of composition B have an apparent density of between about 1.0 and about 1.4 g/cm$^3$.

17. The composition according to claim 1, wherein the A/B quantitative ratio is between about 0.08 and about 5.

18. The composition according to claim 1, wherein the active materials in composition A comprises a pesticide.

19. The composition according to claim 18, wherein the pesticide comprises an insecticide, a nematicide or an acaricide.

20. The composition according to claim 1, wherein the active material in composition A has an LD$_{50}$ of less than about 2000 mg/kg.

21. The composition according to claim 20, wherein the active material in composition A has an LD$_{50}$ of less than about 1550 mg/kg.

22. The composition according to claim 21, wherein the active material in composition A has an LD$_{50}$ of less than about 500 mg/kg.

23. The composition according to claim 1, wherein the granules of compositions A and B have a median diameter of between about 0.200 and about 4 mm.

24. The composition according to claim 1, wherein the granules of compositions A and B have a minimum size greater than about 0.15 mm.

25. The composition according to claim 1, wherein the ratio of the median diameter of the granules of composition A to the median diameter of the granules of composition B is less than or equal to about 2.

26. The composition according to claim 1, wherein the active material content of composition A is between about 5 and about 100%.

27. The composition according to claim 26, wherein the active material content of composition A is between about 50 and about 90%.

28. The composition according to claim 1, wherein the acid/carbonate ratio by weight is between about 0.5 and about 15.

29. The composition according to claim 1, wherein the acid is solid and weak.

30. The composition according to claim 29, wherein the alkaline carbonate is derived from an alkali metal or alkaline-earth metal, or from an ammonium or organoammonium cation.

31. The composition according to claim 30, wherein the alkali metal is sodium or potassium or wherein the alkaline-earth metal is calcium or magnesium.

32. The composition according to claim 30, wherein the alkaline carbonate is derived from an alkali metal.

33. The composition according to claim 29, wherein the acid is a carboxylic, polycarboxylic, phosphoric or phosphonic acid, or a salt or ester thereof having an acidic functional group.

34. The composition according to claim 1, wherein the effervescent agent content of composition B is between about 3 and about 95%.

35. The composition according to claim 34, wherein the effervescent agent content of composition B is between about 5 and about 60%.

36. The composition according to claim 1, wherein the granules of compositions A and B further comprise from about 0.1 to about 10% of a wetting agent, from about 0.3 to about 25% of a dispersing agent, and from about 0 to about 90% of a vehicle or filler which is soluble or insoluble in water.

37. The composition according to claim 1, wherein the granules of compositions A and B further comprise from about 0.5 to about 5% of a wetting agent, from about 2 to about 20% of a dispersing agent, and from about 0 to about 30% of a vehicle or filler which is soluble or insoluble in water.

38. The composition according to claim 1, wherein the granules of compositions A and B have a wettability time of less than about 5 minutes, a degree of dispersibility of greater than about 85%, and a degree of suspensibility of greater than about 50%.

39. The composition according to claim 38, wherein the granules of compositions A and B have a wettability time of less than about 2 minutes, a degree of dispersibility of greater than about 92%, and a degree of suspensibility of greater than about 70%.

* * * * *